(12) United States Patent
Dunki-Jacobs et al.

(10) Patent No.: US 7,983,739 B2
(45) Date of Patent: Jul. 19, 2011

(54) POSITION TRACKING AND CONTROL FOR A SCANNING ASSEMBLY (75) Inventors: Robert J. Dunki-Jacobs, Mason, OH (US); Michael P. Weir, Blanchester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 698 days.

(21) Appl. No.: 11/845,457

(22) Filed: Aug. 27, 2007

(65) Prior Publication Data
US 2009/0062658 A1 Mar. 5, 2009

(51) Int. Cl.
A61B 6/00 (2006.01)
G21F 5/02 (2006.01)
G02B 26/12 (2006.01)

(52) U.S. Cl. .................. 600/476; 250/496.1; 359/224.1

(58) Field of Classification Search .................. 600/476; 359/236
See application file for complete search history.

(56) References Cited

U.S. PATENT DOCUMENTS

| | | |
|---|---|---|
| 3,758,199 A | 9/1973 | Thaxter |
| 3,959,582 A | 5/1976 | Law et al. |
| 4,082,635 A | 4/1978 | Fritz et al. |
| 4,141,362 A | 2/1979 | Wurster |
| 4,313,431 A | 2/1982 | Frank |
| 4,379,039 A | 4/1983 | Fujimoto et al. |
| 4,403,273 A | 9/1983 | Nishioka |
| 4,409,477 A | 10/1983 | Carl |
| 4,421,382 A | 12/1983 | Doi et al. |
| 4,524,761 A | 6/1985 | Hattori et al. |
| 4,527,552 A | 7/1985 | Hattori |
| 4,573,465 A | 3/1986 | Sugiyama et al. |
| 4,576,999 A | 3/1986 | Eckberg |
| 4,597,380 A | 7/1986 | Raif et al. |
| 4,643,967 A | 2/1987 | Bryant |
| 4,676,231 A | 6/1987 | Hisazumi et al. |
| 4,760,840 A | 8/1988 | Fournier, Jr. et al. |
| 4,803,550 A | 2/1989 | Yabe et al. |
| 4,872,458 A | 10/1989 | Kanehira et al. |
| 4,902,083 A | 2/1990 | Wells |
| 4,902,115 A | 2/1990 | Takahashi |
| 4,934,773 A | 6/1990 | Becker |

(Continued)

FOREIGN PATENT DOCUMENTS

DE 3837248 5/1990

(Continued)

OTHER PUBLICATIONS

Kiang, M-H et al., "Surface-Micromachined Electrostatic-Comb Driven Scanning Micromirrors for Barcode Scanners" (date of first publication unknown).

(Continued)

*Primary Examiner* — Tse Chen
*Assistant Examiner* — Hien Nguyen
(74) *Attorney, Agent, or Firm* — Victor C. Moreno (57) ABSTRACT

A scanned beam imaging system including a radiation source configured to provide a beam of radiation, a movable element configured to direct the beam of radiation onto a scanned area, and a collector configured to receive radiation returned from the scanned area. The imaging system further includes a housing that houses the movable element therein and a reference mark coupled to or received in the housing. The reference mark is positioned such that at least part of the radiation from the radiation source is directable at the reference mark.

23 Claims, 9 Drawing Sheets

U.S. PATENT DOCUMENTS

| | | |
|---|---|---|
| 4,938,205 A | 7/1990 | Nudelman |
| 5,003,300 A | 3/1991 | Wells |
| 5,023,905 A | 6/1991 | Wells et al. |
| 5,048,077 A | 9/1991 | Wells et al. |
| 5,074,860 A | 12/1991 | Gregory et al. |
| 5,078,150 A | 1/1992 | Hara et al. |
| 5,163,936 A | 11/1992 | Black et al. |
| 5,163,945 A | 11/1992 | Ortiz et al. |
| 5,172,685 A | 12/1992 | Nudelman |
| 5,192,288 A | 3/1993 | Thompson et al. |
| 5,200,819 A | 4/1993 | Nudelman et al. |
| 5,200,838 A | 4/1993 | Nudelman et al. |
| 5,207,670 A | 5/1993 | Sinofsky |
| 5,218,195 A | 6/1993 | Hakamata |
| 5,251,025 A | 10/1993 | Cooper et al. |
| 5,251,613 A | 10/1993 | Adair |
| 5,269,289 A | 12/1993 | Takehana et al. |
| 5,318,024 A | 6/1994 | Kittrell et al. |
| 5,334,991 A | 8/1994 | Wells et al. |
| 5,368,015 A | 11/1994 | Wilk |
| 5,370,643 A | 12/1994 | Krivoshlykov et al. |
| 5,387,197 A | 2/1995 | Smith et al. |
| 5,393,647 A | 2/1995 | Neukermans et al. |
| 5,436,655 A | 7/1995 | Hiyama et al. |
| 5,467,104 A | 11/1995 | Furness, III et al. |
| 5,488,862 A | 2/1996 | Neukermans et al. |
| 5,531,740 A | 7/1996 | Black |
| 5,545,211 A | 8/1996 | An et al. |
| 5,552,452 A | 9/1996 | Khadem et al. |
| 5,557,444 A | 9/1996 | Melville et al. |
| 5,590,660 A | 1/1997 | MacAulay et al. |
| 5,596,339 A | 1/1997 | Furness, III et al. |
| 5,608,451 A | 3/1997 | Konno et al. |
| 5,629,790 A | 5/1997 | Neukermans et al. |
| 5,648,618 A | 7/1997 | Neukermans et al. |
| 5,649,952 A | 7/1997 | Lam |
| 5,657,165 A | 8/1997 | Karpman et al. |
| 5,658,710 A | 8/1997 | Neukermans |
| 5,659,327 A | 8/1997 | Furness, III et al. |
| 5,694,237 A | 12/1997 | Melville |
| 5,701,132 A | 12/1997 | Kollin et al. |
| 5,713,891 A | 2/1998 | Poppas |
| 5,728,121 A | 3/1998 | Bimbo et al. |
| 5,735,792 A | 4/1998 | Vanden Hoek et al. |
| 5,742,419 A | 4/1998 | Dickensheets et al. |
| 5,742,421 A | 4/1998 | Wells et al. |
| 5,751,465 A | 5/1998 | Melville et al. |
| 5,768,461 A | 6/1998 | Svetkoff et al. |
| 5,797,944 A | 8/1998 | Nobles et al. |
| 5,817,061 A | 10/1998 | Goodwin et al. |
| 5,823,943 A | 10/1998 | Tomioka et al. |
| 5,827,176 A | 10/1998 | Tanaka et al. |
| 5,827,190 A | 10/1998 | Palcic et al. |
| 5,841,553 A | 11/1998 | Neukermans |
| 5,861,549 A | 1/1999 | Neukermans et al. |
| 5,867,297 A | 2/1999 | Kiang et al. |
| 5,895,866 A | 4/1999 | Neukermans et al. |
| 5,903,397 A | 5/1999 | Melville et al. |
| 5,907,425 A | 5/1999 | Dickensheets et al. |
| 5,913,591 A | 6/1999 | Melville |
| 5,947,930 A | 9/1999 | Schwemberger et al. |
| 5,969,465 A | 10/1999 | Neukermans et al. |
| 5,969,871 A | 10/1999 | Tidwell et al. |
| 5,982,528 A | 11/1999 | Melville |
| 5,982,555 A | 11/1999 | Melville et al. |
| 5,993,037 A | 11/1999 | Tomioka et al. |
| 5,995,264 A | 11/1999 | Melville |
| 6,007,208 A | 12/1999 | Dickensheets et al. |
| 6,008,781 A | 12/1999 | Furness, III et al. |
| 6,013,025 A | 1/2000 | Bonne et al. |
| 6,016,440 A | 1/2000 | Simon et al. |
| 6,017,356 A | 1/2000 | Frederick et al. |
| 6,017,603 A | 1/2000 | Tokuda et al. |
| 6,024,744 A | 2/2000 | Kese et al. |
| 6,043,799 A | 3/2000 | Tidwell |
| 6,044,705 A | 4/2000 | Neukermans et al. |
| 6,046,720 A | 4/2000 | Melville et al. |
| 6,049,407 A | 4/2000 | Melville |
| 6,056,721 A | 5/2000 | Shulze |
| 6,057,952 A | 5/2000 | Kubo et al. |
| 6,059,720 A | 5/2000 | Furusawa et al. |
| 6,061,163 A | 5/2000 | Melville |
| 6,064,779 A | 5/2000 | Neukermans et al. |
| 6,069,725 A | 5/2000 | Melville |
| 6,086,528 A | 7/2000 | Adair |
| 6,086,531 A | 7/2000 | Tomioka et al. |
| 6,088,145 A | 7/2000 | Dickensheets et al. |
| 6,097,353 A | 8/2000 | Melville et al. |
| 6,122,394 A | 9/2000 | Neukermans et al. |
| 6,139,175 A | 10/2000 | Tomioka et al. |
| 6,140,979 A | 10/2000 | Gerhard et al. |
| 6,151,167 A | 11/2000 | Melville |
| 6,154,305 A | 11/2000 | Dickensheets et al. |
| 6,154,321 A | 11/2000 | Melville et al. |
| 6,157,352 A | 12/2000 | Kollin et al. |
| 6,166,841 A | 12/2000 | Melville |
| 6,172,789 B1 | 1/2001 | Kino et al. |
| 6,178,346 B1 | 1/2001 | Amundson et al. |
| 6,179,776 B1 | 1/2001 | Adams et al. |
| 6,191,761 B1 | 2/2001 | Melville et al. |
| 6,192,267 B1 | 2/2001 | Scherninski et al. |
| 6,200,595 B1 | 3/2001 | Motoyashiki et al. |
| 6,204,829 B1 | 3/2001 | Tidwell |
| 6,204,832 B1 | 3/2001 | Melville et al. |
| 6,207,392 B1 | 3/2001 | Weiss et al. |
| 6,210,401 B1 | 4/2001 | Lai |
| 6,220,711 B1 | 4/2001 | Melville |
| 6,221,068 B1 | 4/2001 | Fried et al. |
| 6,229,139 B1 | 5/2001 | Neukermans et al. |
| 6,235,017 B1 | 5/2001 | Jegorov et al. |
| 6,243,186 B1 | 6/2001 | Melville |
| 6,245,590 B1 | 6/2001 | Wine et al. |
| 6,256,131 B1 | 7/2001 | Wine et al. |
| 6,257,727 B1 | 7/2001 | Melville |
| 6,272,907 B1 | 8/2001 | Neukermans et al. |
| 6,276,798 B1 | 8/2001 | Gil et al. |
| 6,281,862 B1 | 8/2001 | Tidwell et al. |
| 6,284,185 B1 | 9/2001 | Tokuda et al. |
| 6,285,489 B1 | 9/2001 | Helsel et al. |
| 6,285,505 B1 | 9/2001 | Melville et al. |
| 6,288,816 B1 | 9/2001 | Melville et al. |
| 6,292,287 B1 | 9/2001 | Fujinoki |
| 6,293,911 B1 | 9/2001 | Imaizumi et al. |
| 6,294,239 B1 | 9/2001 | Tokuda et al. |
| 6,294,775 B1 | 9/2001 | Seibel et al. |
| 6,317,103 B1 | 11/2001 | Furness, III et al. |
| 6,323,037 B1 | 11/2001 | Lauto et al. |
| 6,324,007 B1 | 11/2001 | Melville |
| 6,327,493 B1 | 12/2001 | Ozawa et al. |
| 6,331,909 B1 | 12/2001 | Dunfield |
| 6,333,110 B1 | 12/2001 | Barbera-Guillem |
| 6,338,641 B2 | 1/2002 | Nicholls |
| 6,352,344 B2 | 3/2002 | Tidwell |
| 6,353,183 B1 | 3/2002 | Ott et al. |
| 6,362,912 B1 | 3/2002 | Lewis et al. |
| 6,364,829 B1 | 4/2002 | Fulghum |
| 6,369,928 B1 | 4/2002 | Mandella et al. |
| 6,369,953 B2 | 4/2002 | Melville et al. |
| 6,369,954 B1 | 4/2002 | Berge et al. |
| 6,370,406 B1 | 4/2002 | Wach et al. |
| 6,370,422 B1 | 4/2002 | Richards-Kortum et al. |
| 6,373,995 B1 | 4/2002 | Moore |
| 6,384,406 B1 | 5/2002 | Wine et al. |
| 6,388,641 B2 | 5/2002 | Tidwell et al. |
| 6,392,220 B1 | 5/2002 | Slater et al. |
| 6,396,461 B1 | 5/2002 | Lewis et al. |
| 6,414,779 B1 | 7/2002 | Mandella et al. |
| 6,417,502 B1 | 7/2002 | Stoner et al. |
| 6,423,956 B1 | 7/2002 | Mandella et al. |
| 6,425,900 B1 | 7/2002 | Knodel et al. |
| 6,426,013 B1 | 7/2002 | Neukermans et al. |
| 6,433,907 B1 | 8/2002 | Lippert et al. |
| 6,435,637 B1 | 8/2002 | Lyman |
| 6,441,356 B1 | 8/2002 | Mandella et al. |
| 6,445,362 B1 | 9/2002 | Tegreene |
| 6,447,524 B1 | 9/2002 | Knodel et al. |
| 6,462,770 B1 | 10/2002 | Cline et al. |

| Patent No. | Date | Inventor |
|---|---|---|
| 6,464,363 B1 | 10/2002 | Nishioka et al. |
| 6,467,345 B1 | 10/2002 | Neukermans et al. |
| 6,470,124 B1 | 10/2002 | Le Gargasson et al. |
| 6,477,403 B1 | 11/2002 | Eguchi et al. |
| 6,478,809 B1 | 11/2002 | Brotz |
| 6,485,413 B1 | 11/2002 | Boppart et al. |
| 6,492,962 B2 | 12/2002 | Melville et al. |
| 6,494,578 B1 | 12/2002 | Plummer et al. |
| 6,503,196 B1 | 1/2003 | Kehr et al. |
| 6,510,338 B1 | 1/2003 | Irion et al. |
| 6,512,622 B2 | 1/2003 | Wine et al. |
| 6,513,939 B1 | 2/2003 | Fettig et al. |
| 6,515,278 B2 | 2/2003 | Wine et al. |
| 6,515,781 B2 | 2/2003 | Lewis et al. |
| 6,520,972 B2 | 2/2003 | Peters |
| 6,522,444 B2 | 2/2003 | Mandella et al. |
| 6,525,310 B2 | 2/2003 | Dunfield |
| 6,527,708 B1 | 3/2003 | Nakamura et al. |
| 6,529,770 B1 | 3/2003 | Grimblatov |
| 6,530,698 B1 | 3/2003 | Kuhara et al. |
| 6,535,183 B2 | 3/2003 | Melville et al. |
| 6,535,325 B2 | 3/2003 | Helsel et al. |
| 6,537,211 B1 | 3/2003 | Wang et al. |
| 6,538,625 B2 | 3/2003 | Tidwell et al. |
| 6,545,260 B1 | 4/2003 | Katashiro et al. |
| 6,560,028 B2 | 5/2003 | Melville et al. |
| 6,563,105 B2 | 5/2003 | Seibel et al. |
| 6,563,106 B1 | 5/2003 | Bowers et al. |
| 6,572,606 B2 | 6/2003 | Kliewer et al. |
| 6,583,117 B2 | 6/2003 | Owen et al. |
| 6,583,772 B1 | 6/2003 | Lewis et al. |
| 6,585,642 B2 | 7/2003 | Christopher |
| 6,603,552 B1 | 8/2003 | Cline et al. |
| 6,608,297 B2 | 8/2003 | Neukermans et al. |
| 6,639,570 B2 | 10/2003 | Furness, III et al. |
| 6,639,719 B2 | 10/2003 | Tegreene et al. |
| 6,650,877 B1 | 11/2003 | Tarbouriech et al. |
| 6,653,621 B2 | 11/2003 | Wine et al. |
| 6,654,158 B2 | 11/2003 | Helsel et al. |
| 6,661,393 B2 | 12/2003 | Tegreene et al. |
| 6,674,993 B1 | 1/2004 | Tarbouriech |
| 6,685,804 B1 | 2/2004 | Ikeda et al. |
| 6,687,034 B2 | 2/2004 | Wine et al. |
| 6,689,056 B1 | 2/2004 | Kilcoyne et al. |
| 6,699,170 B1 | 3/2004 | Crocker et al. |
| 6,700,552 B2 | 3/2004 | Kollin et al. |
| 6,714,331 B2 | 3/2004 | Lewis et al. |
| 6,734,835 B2 | 5/2004 | Tidwell et al. |
| 6,736,511 B2 | 5/2004 | Plummer et al. |
| 6,741,884 B1 | 5/2004 | Freeman et al. |
| 6,749,346 B1 | 6/2004 | Dickensheets et al. |
| 6,755,536 B2 | 6/2004 | Tegreene et al. |
| 6,762,867 B2 | 7/2004 | Lippert et al. |
| 6,768,588 B2 | 7/2004 | Urey |
| 6,771,001 B2 | 8/2004 | Mao et al. |
| 6,782,748 B2 | 8/2004 | Weber et al. |
| 6,786,382 B1 | 9/2004 | Hoffman |
| 6,795,221 B1 | 9/2004 | Urey |
| 6,802,809 B2 | 10/2004 | Okada |
| 6,803,561 B2 | 10/2004 | Dunfield |
| 6,821,245 B2 | 11/2004 | Cline et al. |
| 6,845,190 B1 | 1/2005 | Smithwick et al. |
| 6,856,436 B2 | 2/2005 | Brukilacchio et al. |
| 6,856,712 B2 | 2/2005 | Fauver et al. |
| 6,879,428 B2 | 4/2005 | Massieu |
| 6,888,552 B2 | 5/2005 | Debevec et al. |
| 6,894,823 B2 | 5/2005 | Taylor et al. |
| 6,899,675 B2 | 5/2005 | Cline et al. |
| 6,902,527 B1 | 6/2005 | Doguchi et al. |
| 6,905,057 B2 | 6/2005 | Swayze et al. |
| 6,939,364 B1 | 9/2005 | Soltz et al. |
| 6,957,898 B2 | 10/2005 | Yu |
| 6,967,757 B1 | 11/2005 | Allen et al. |
| 6,974,472 B2 | 12/2005 | Hong et al. |
| 6,975,898 B2 | 12/2005 | Seibel et al. |
| 6,976,994 B2 | 12/2005 | Ballou et al. |
| 6,978,921 B2 | 12/2005 | Shelton, IV et al. |
| 6,985,271 B2 | 1/2006 | Yazdi et al. |
| 6,991,602 B2 | 1/2006 | Nakazawa et al. |
| 7,005,195 B2 | 2/2006 | Cheng et al. |
| 7,009,634 B2 | 3/2006 | Iddan et al. |
| 7,013,730 B2 | 3/2006 | Malametz |
| 7,015,956 B2 | 3/2006 | Luo et al. |
| 7,018,401 B1 | 3/2006 | Hyodoh et al. |
| 7,023,402 B2 | 4/2006 | Lewis et al. |
| 7,025,777 B2 | 4/2006 | Moore |
| 7,033,348 B2 | 4/2006 | Alfano et al. |
| 7,035,777 B2 | 4/2006 | Araki et al. |
| 7,061,450 B2 | 6/2006 | Bright et al. |
| 7,065,301 B2 | 6/2006 | Shastri et al. |
| 7,066,879 B2 | 6/2006 | Fowler et al. |
| 7,071,594 B1 | 7/2006 | Yan et al. |
| 7,071,931 B2 | 7/2006 | Tegreene et al. |
| 7,078,378 B1 | 7/2006 | Owen et al. |
| 7,108,656 B2 | 9/2006 | Fujikawa et al. |
| 7,112,302 B2 | 9/2006 | Yoshimi et al. |
| 7,126,903 B2 | 10/2006 | Feenstra et al. |
| 7,189,961 B2 | 3/2007 | Johnston et al. |
| 7,190,329 B2 | 3/2007 | Lewis et al. |
| 7,232,071 B2 | 6/2007 | Lewis et al. |
| 7,271,383 B2 | 9/2007 | Chee |
| 7,391,013 B2 | 6/2008 | Johnston et al. |
| 2001/0055462 A1 | 12/2001 | Seibel |
| 2002/0015724 A1 | 2/2002 | Yang et al. |
| 2002/0024495 A1 | 2/2002 | Lippert et al. |
| 2002/0050956 A1 | 5/2002 | Gerhard et al. |
| 2002/0075284 A1 | 6/2002 | Rabb, III |
| 2002/0088925 A1 | 7/2002 | Nestorovic et al. |
| 2002/0115922 A1 | 8/2002 | Waner et al. |
| 2002/0141026 A1 | 10/2002 | Wiklof et al. |
| 2002/0158814 A1 | 10/2002 | Bright et al. |
| 2002/0163484 A1 | 11/2002 | Furness, III et al. |
| 2002/0167462 A1 | 11/2002 | Lewis et al. |
| 2002/0171776 A1 | 11/2002 | Tegreene et al. |
| 2002/0171937 A1 | 11/2002 | Tegreene et al. |
| 2003/0016187 A1 | 1/2003 | Melville et al. |
| 2003/0030753 A1 | 2/2003 | Kondo et al. |
| 2003/0032143 A1 | 2/2003 | Neff et al. |
| 2003/0034709 A1 | 2/2003 | Jerman |
| 2003/0058190 A1 | 3/2003 | Lewis et al. |
| 2003/0086172 A1 | 5/2003 | Urey |
| 2003/0092995 A1 | 5/2003 | Thompson |
| 2003/0130562 A1 | 7/2003 | Barbato et al. |
| 2003/0142934 A1 | 7/2003 | Pan et al. |
| 2003/0159447 A1 | 8/2003 | Sergio et al. |
| 2003/0214460 A1 | 11/2003 | Kovacs |
| 2003/0216729 A1 | 11/2003 | Marchitto et al. |
| 2004/0004585 A1 | 1/2004 | Brown et al. |
| 2004/0057103 A1 | 3/2004 | Bernstein |
| 2004/0075624 A1 | 4/2004 | Tegreene et al. |
| 2004/0076390 A1 | 4/2004 | Dong Yang et al. |
| 2004/0085261 A1 | 5/2004 | Lewis et al. |
| 2004/0085617 A1 | 5/2004 | Helsel et al. |
| 2004/0087844 A1 | 5/2004 | Yen |
| 2004/0101822 A1 | 5/2004 | Wiesner et al. |
| 2004/0113059 A1 | 6/2004 | Kawano et al. |
| 2004/0118821 A1 | 6/2004 | Han et al. |
| 2004/0119004 A1 | 6/2004 | Wine et al. |
| 2004/0122328 A1 | 6/2004 | Wang et al. |
| 2004/0133786 A1 | 7/2004 | Tarbouriech |
| 2004/0151466 A1 | 8/2004 | Crossman-Bosworth et al. |
| 2004/0155186 A1 | 8/2004 | Nestorovic et al. |
| 2004/0155834 A1 | 8/2004 | Wit et al. |
| 2004/0179254 A1 | 9/2004 | Lewis et al. |
| 2004/0196518 A1 | 10/2004 | Wine et al. |
| 2004/0223202 A1 | 11/2004 | Lippert et al. |
| 2004/0225222 A1 | 11/2004 | Zeng et al. |
| 2004/0236371 A1 | 11/2004 | McNally-Heintzelman et al. |
| 2004/0240866 A1 | 12/2004 | Ramsbottom |
| 2004/0252377 A1 | 12/2004 | Urey |
| 2004/0254474 A1 | 12/2004 | Seibel et al. |
| 2005/0010787 A1 | 1/2005 | Tarbouriech |
| 2005/0014995 A1 | 1/2005 | Amundson et al. |
| 2005/0020877 A1* | 1/2005 | Ishihara et al. ............... 600/109 |
| 2005/0020926 A1 | 1/2005 | Wiklof et al. |
| 2005/0023356 A1* | 2/2005 | Wiklof et al. ............ 235/462.42 |
| 2005/0030305 A1 | 2/2005 | Brown et al. |
| 2005/0038322 A1 | 2/2005 | Banik |

| | | | |
|---|---|---|---|
| 2005/0116038 A1 | 6/2005 | Lewis et al. | |
| 2005/0162762 A1 | 7/2005 | Novak | |
| 2005/0187441 A1 | 8/2005 | Kawasaki et al. | |
| 2005/0203343 A1 | 9/2005 | Kang et al. | |
| 2005/0240147 A1 | 10/2005 | Makower et al. | |
| 2006/0010985 A1 | 1/2006 | Schneider | |
| 2006/0084867 A1 | 4/2006 | Tremblay et al. | |
| 2006/0164330 A1 | 7/2006 | Bright et al. | |
| 2006/0183246 A1 | 8/2006 | Wiesner et al. | |
| 2006/0195014 A1 | 8/2006 | Seibel et al. | |
| 2006/0238774 A1 | 10/2006 | Lindner et al. | |
| 2006/0245971 A1 | 11/2006 | Burns et al. | |
| 2006/0284790 A1 | 12/2006 | Tegreene et al. | |
| 2007/0038119 A1 | 2/2007 | Chen et al. | |
| 2007/0046778 A1 | 3/2007 | Ishihara et al. | |
| 2007/0135770 A1 | 6/2007 | Hunt et al. | |
| 2007/0156021 A1 | 7/2007 | Morse et al. | |
| 2007/0161876 A1 | 7/2007 | Bambot et al. | |
| 2007/0162093 A1 | 7/2007 | Porter et al. | |
| 2007/0167681 A1 | 7/2007 | Gill et al. | |
| 2007/0173707 A1 | 7/2007 | Mitra | |
| 2007/0179366 A1 | 8/2007 | Pewzner et al. | |
| 2007/0197874 A1 | 8/2007 | Ishihara | |
| 2007/0197875 A1 | 8/2007 | Osaka | |
| 2007/0203413 A1 | 8/2007 | Frangioni | |
| 2007/0213588 A1 | 9/2007 | Morishita et al. | |
| 2007/0213618 A1 | 9/2007 | Li et al. | |
| 2007/0225695 A1 | 9/2007 | Mayer et al. | |
| 2007/0238930 A1 | 10/2007 | Wiklof et al. | |
| 2007/0244365 A1 | 10/2007 | Wiklof | |
| 2007/0260121 A1 | 11/2007 | Bakos et al. | |
| 2007/0260273 A1 | 11/2007 | Cropper et al. | |
| 2008/0058629 A1 | 3/2008 | Seibel et al. | |

FOREIGN PATENT DOCUMENTS

| | | |
|---|---|---|
| EP | 1139141 | 10/2001 |
| EP | 1716802 | 11/2006 |
| EP | 1747751 | 1/2007 |
| EP | 1797813 | 6/2007 |
| JP | 2007-244590 | 9/2007 |
| JP | 2007-244680 | 9/2007 |
| WO | WO 98/13720 | 4/1998 |
| WO | WO 99/18456 | 4/1999 |
| WO | 99/58930 | 11/1999 |
| WO | 00/13210 | 3/2000 |
| WO | 01/10322 | 2/2001 |
| WO | 01/60274 | 8/2001 |
| WO | 02/062239 | 8/2002 |
| WO | WO 03/069380 | 8/2003 |
| WO | 03/088643 | 10/2003 |
| WO | 03/098918 | 11/2003 |
| WO | 03/101287 | 11/2003 |
| WO | 2006/020605 | 2/2006 |
| WO | WO 2006/049787 | 5/2006 |
| WO | WO 2006/055733 | 5/2006 |
| WO | 2007/041542 | 4/2007 |
| WO | 2007/070831 | 6/2007 |
| WO | WO 2007/067163 | 6/2007 |
| WO | WO 2007/084915 | 7/2007 |

OTHER PUBLICATIONS

Lewis, J.R. et al., "Scanned beam medical imager," MOEMS Display and Imaging Systems II, Proceedings of SPIE vol. 5348, pp. 40-51 (2004).
James, R. et al., "Update on MEMS-based Scanned Beam Imager" (date of first publication unknown).
Wiklof, C., "Display technology spawns laser camera," Laser Focus World (Dec. 2004).
"Press Information—Phillips' Fluid Lenses Bring Things into Focus," http://www.newscenter.philips.corn (Mar. 3, 2004).
Lettice, J., "The $5 'no moving parts' fluid zoom lens—twice," The Register (Mar. 15, 2004).
"Volcano Products—IVUS Imaging Visions® PV018," http://www.volcanotherapeutics.com (date of first publication unknown).
Barhoum, E.S. et al., "Optical modeling of an ultrathin scanning fiber endoscope, a preliminary study of confocal versus non-confocal detection," Optics Express, vol. 13, No. 19, pp. 7548-7652 (Sep. 19, 2005).
"Crystalplex Technology—PlxBead™ Superior Qualities," http:www.crystalplex.com (date of first publication unknown).
"Microvision [illuminating information] Products/Overview, Corporate Overview Presentation 2006" (2006).
"Holographic Beam Combiner for Ladar, Printer, Fiber Optics, Cancer Treatment," by Digital and Optics Technologies, Inc., http://www.mdatechnology.net (date of first publication unknown).
Brown, D.M., Abstract from SPIE Digital Library for "High-power laser diode beam combiner," Optical Engineering, vol. 42, Issue 11 (2003).
Literature entitled "All fiber beam combiner from Point Source" (Oct. 13, 2006).
"Custom Polarzing Cube Beamsplitters," from GlobalSpec The Engineering Search Engine, http://www.globalspec.com (date of first publication unknown).
Literature entitled "Dallas Semiconductor MAXIM—Visible-Laser Driver has Digitally Controlled Power Modulation," by Maxim Integrated Products, http://www.maxim-ic.com (Jul. 1, 2001).
"SCAN Mode Strategies for SCUBA-2" (May 25, 2005).
Seifert, M. et al., "High Power Diode Laser Beam Scanning in Multi-Kilowatt Range," Proceedings of the 23rd International Congress on Applications of Lasers and Electro-Optics (2004).
Jutzi, B. et al., "Sub-Pixel Edge Localization Based on Laser Waveform Analysis," ISPRS WG III/3, III/4, V/3 Workshop "Laser scanning 2005," Enschede, the Netherlands (Sep. 12-14, 2005).
"Bladeless Trocars," Johnson & Johnson, http://www.jnjgateway.com (date of first publication unknown).
Yeh, R. et al., "Microelectromechanical Components for Articulated Microrobots" (date of first publication unknown).
Xu, Q. et al., "Micrometre-scale silicon electro-optic modulator," Nature, vol. 435, pp. 325-327 (May 19, 2005).
Park, H. et al., "Development of Double-Sided Silicon Strip Position Sensor," 2005 IEEE Nuclear Science Symposium Conference Record, pp. 781-785 (2005).
Hammond, S.W., "Architecture and Operation of a Systolic Sparse Matrix Engine," Proceedings of the 3rd SIAM Conference on Parallel Processing for Scientific Computing, pp. 419-423 (1987).
Ra, H. et al., "Biomedical Optics & Medical Imaging—Microtechnology enables endoscopic confocal microscopy," SPIE (http://spie.org) (2007).
Invitation to Pay Additional Fees with Partial International Search Report, PCT/US2008/074275 (Jan. 16, 2009).
Invitation to Pay Additional Fees with Partial International Search Report, PCT/US2008/074273 (Dec. 30, 2008).
International Search Report issued regarding International Application No. PCT/US2007/078868 (Mar. 28, 2008).
PCT, International Search Report, PCT/US2008/056589 (Jul. 30, 2008).
PCT, International Search Report, PCT/US2008/059231 (Jul. 4, 2008).
PCT, International Search Report, PCT/US2007/087923 (May 21, 2008).
PCT, International Search Report, PCT/US2008/056596 (Jun. 23, 2008).
PCT, International Search Report, PCT/US2008/059235 (Jul. 14, 2008).
PCT, International Search Report, PCT/US2007/087930 (Jul. 3, 2008).
PCT, International Search Report, PCT/US2008/051274 (Jul. 18, 2008).
PCT, International Search Report, PCT/US2008/066552 (Oct. 23, 2008).
PCT, International Search Report and Written Opinion, International Application No. PCT/US2008/074273 (Mar. 10, 2009).
PCT, International Preliminary Report on Patentability, International Application No. PCT/US2008/074273 (Mar. 11, 2010).

* cited by examiner

POSITION TRACKING AND CONTROL FOR A SCANNING ASSEMBLY

The present application is directed to imaging devices, and more particularly, to imaging devices utilizing scanned beam imaging technology.

BACKGROUND

Imaging devices may be used to provide visualization of a site on or within a patient, or in other areas of use. One such device is described in U.S. Patent Publication Number 2005/0020926; corresponding to U.S. application Ser. No. 10/873,540, filed on Jun. 21, 2004, the entire contents of which are hereby incorporated by reference as if fully set forth herein. In such systems a scanned beam imaging system may utilize a radiation source. The radiation is scanned onto or across a scanned area by an oscillating mirror. The radiation is reflected, scattered, refracted or otherwise perturbed by the illuminated area. The perturbed radiation is then gathered/sensed and converted into electrical signals that are processed to generate a viewable image.

SUMMARY

In one embodiment the present invention is a method and device for determining the position of the movable element to thereby track the position of the reflected beam. More particularly, in one embodiment the invention is a scanned beam imaging system including a radiation source configured to provide a beam of radiation, a movable element configured to direct the beam of radiation onto a scanned area, and a collector configured to receive radiation returned from the scanned area. The imaging system further includes a housing that houses the movable element therein and a reference mark coupled to or received in the housing. The reference mark is positioned such that at least part of the radiation from the radiation source is directable at the reference mark.

In another embodiment the invention is a microelectrical mechanical system including a movable element and a driving component for moving the movable element in an oscillating manner. The system further includes an offset means for providing an initial offset of the movable element such that the moveable element is not coplanar with the driving component in the absence of any forces applied by the driving component.

The details of one or more embodiments of the invention are set forth in the accompanying drawings and the description below. Other features, objects, and advantages of the invention will be apparent from the description and the drawings, and from the claims.

DETAILED DESCRIPTION

Before explaining the several expressions of embodiments of the present invention in detail, it should be noted that each is not limited in its application or use to the details of construction and arrangement of parts illustrated in the accompanying drawings and description. The illustrative expressions of embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is further understood that any one or more of the following-described expressions of embodiments, examples, etc. can be combined with any one or more of the other following-described expressions of embodiments, examples, etc.

Figure 1:
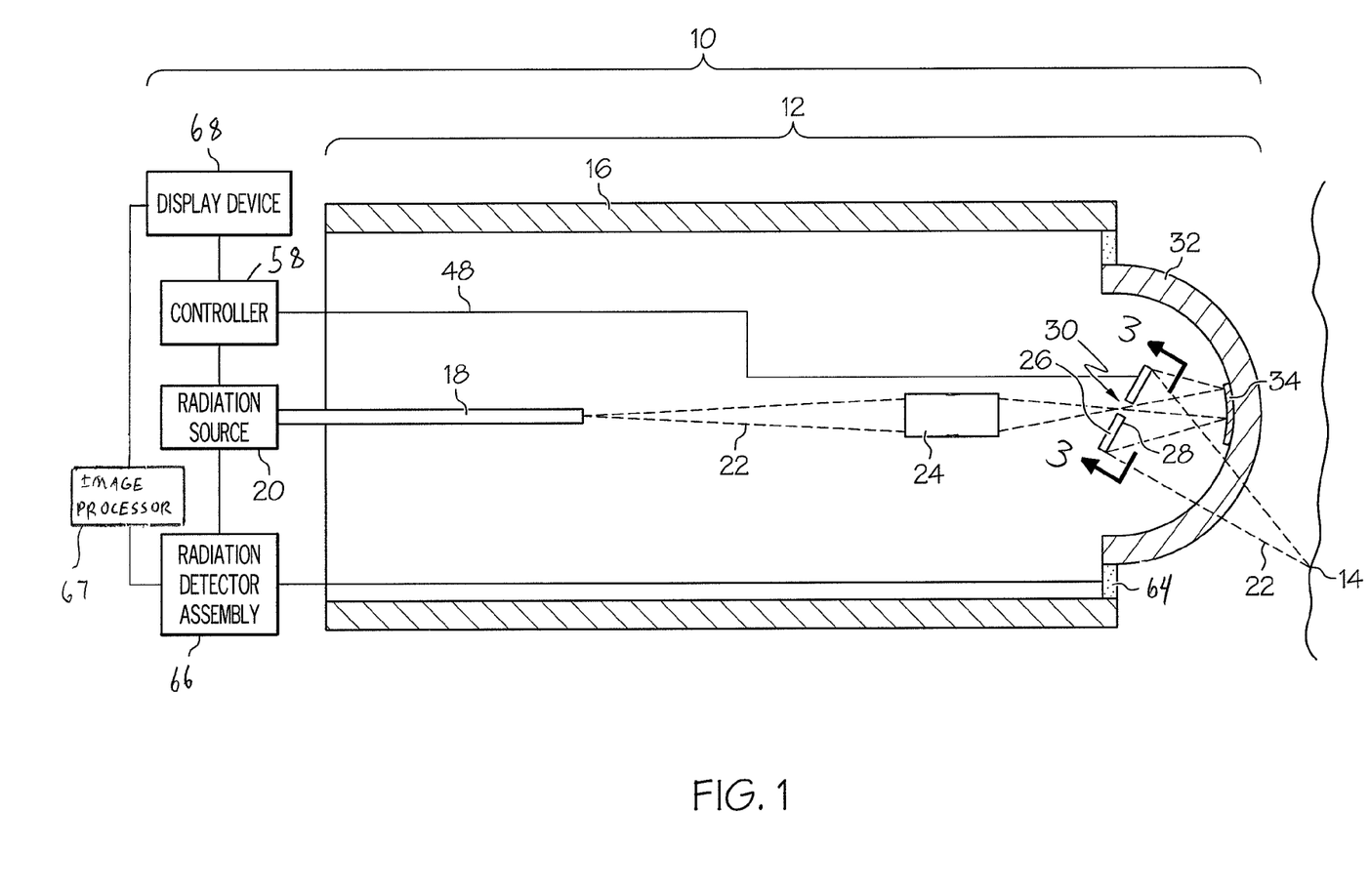
FIG. 1 is a side cross section and schematic representation of one embodiment of a scanning assembly.

As shown in FIG. 1, a scanning assembly, generally designated 10, may include a scanning unit 12 configured direct radiation onto a scanned area/illuminated area/area of interest 14. The scanned area 14 may be part of or positioned on or inside the body of a human or animal patient, but could also be any area which is desired to be scanned/visualized (in some cases excluding any portions of the scanning assembly 10). The scanning unit 12 (or other components or subcomponents) can then detect the radiation that is reflected, scattered, refracted or otherwise perturbed or affected (hereinafter referred to as radiation that is "returned from" the illuminated area 14) by the area 14 receiving radiation. The detected radiation can then be analyzed and processed to generate an image of the illuminated area 14.

The scanning unit 12 includes a housing 16 which receives a source fiber 18 therein. In the illustrated embodiment the housing 16 is generally cylindrical (see FIG. 2) and sized to be gripped and manually manipulated, although the housing 16 can take any of a variety of forms, shapes and sizes. The source fiber 18 is operatively coupled to a radiation source 20 to transmit radiation from the radiation source 20 to a position inside of the housing 16 or adjacent to a reflector 26. The radiation source 20 can take any of a variety of forms, including light emitting diodes (LEDs), lasers, thermal sources, arc sources, fluorescent sources, gas discharge sources, other sources, or combinations of these sources. The radiation provided by the radiation source 20 can include energy in the visible light spectrum, such as red, green, or blue radiation, or various combinations thereof, although the radiation need not necessarily be within the visible spectrum. The source fiber 18 may take the form of one or more optical fibers, or various other energy transmission means sufficient to transmit radiation from the radiation source 20.

The end of the source fiber 18 may be shaped or polished to create a beam 22 of known divergence. After exiting the source fiber 18 the beam 22 may pass through, and be shaped by a lens or other optics 24 (which are optional) to create a desired beam shape. The scanning unit 12 includes the mirror or reflector (or a movable element) 26 at or adjacent to its distal end. The reflector 26 may take the form of a micromirror or other reflective surface. The reflector 26 thus may take the form of or include a microelectrical mechanical system ("MEMS") manufactured using standard MEMS techniques. The reflector 26 may include a semiconductor substrate, such as silicon, with a reflective outer surface, such as gold or other suitable material, forming its outer reflective surface 28. However the reflector 26 may take various other forms, such as a multilayer dielectric coating.

In the illustrated embodiment the reflector 26 includes a central aperture 30 that is positioned to allow the beam 22 to pass therethrough. However, the reflector 26 and scanning unit 12 can take any of a variety of shapes and configurations besides that shown herein. For example, rather than including a central aperture 30 that allows the beam 22 to pass therethrough, the beam 22 may be laterally offset from the reflector 26, and guided to the reflector 26 by another mirror/reflector.

After passing through the aperture 30 of the reflector 26 the beam 22 approaches an optical element 32 that is positioned at a distal end of the scanning unit 12. The optical element 32 can be generally hemispherical and is typically referred to as a dome. However, the shape, curvature, contour, and surface treatment of the optical element 32 may vary depending on the desired application/use of the scanning unit 12 and the desired optical properties of the optical element 32. The optical element 32 may form a hermetic seal with the housing 16 to protect the internal elements of the scanning unit 12 from the surrounding environment.

The optical element 32 may include a reflecting surface 34 on its inner surface. The reflecting surface 34 may be directly deposited on the inner surface of the optical element 32, or integrated into the optical element 32, or can take the form of a separate and discrete element coupled to the optical element 32. After the beam 22 passes through the aperture 30 of the reflector 26, the beam 22 impinges upon the reflecting surface 34 which reflects the beam 22 and re-directs the beam 22 toward the reflector 26. The inner surface of the optical element 32 and/or the reflecting surface 34 may also shape the beam 22 as desired due to the shape or curvature of the reflecting surface 34. If the beam 22 is laterally offset from the center of the scanning unit 12 in the arrangement briefly described above, the reflecting surface 34 on the optical element 32 may be omitted.

Figure 3:
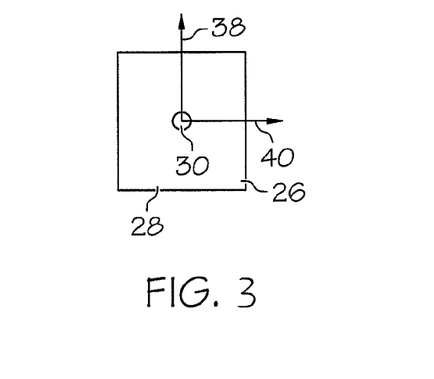
FIG. 3 is a front view taken along line 3-3 of FIG. 1.
Figure 4:
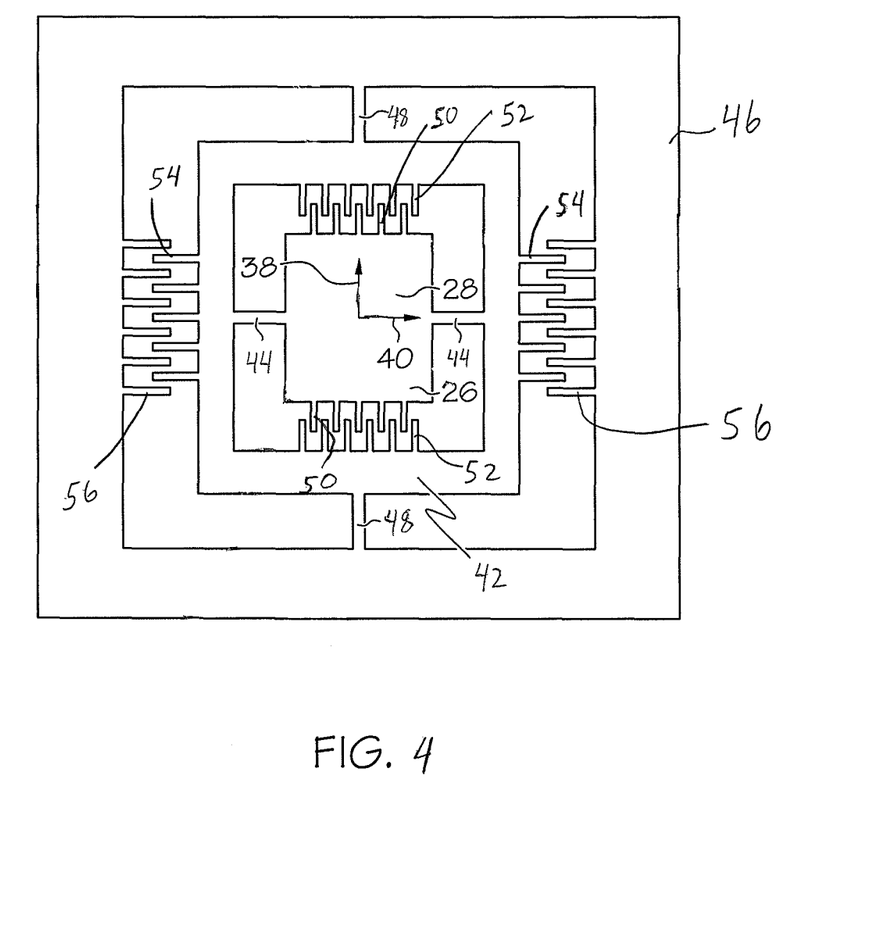
FIG. 4 is a front view of a drive mechanism usable with the scanning assembly of FIG. 1.
Figure 6:
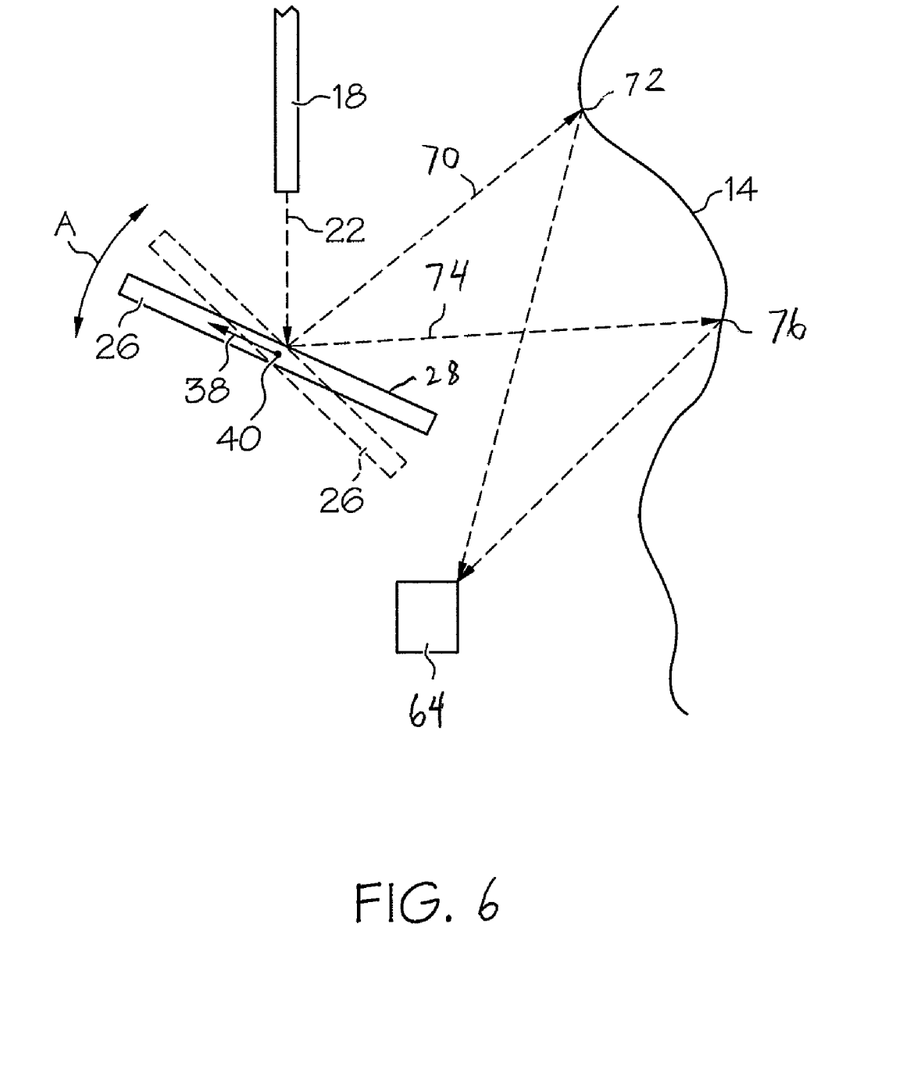
FIG. 6 is a schematic representation of radiation reflected by a reflector at two different positions.

The reflector 26 may be independently oscillatable/movable about two orthogonal axes, such as axes 38, 40 shown in FIGS. 3, 4 and 6. As shown in FIG. 4, the reflector 26 may be rotationally coupled to an inner support structure 42 by a pair of opposed, generally aligned torsion arms 44. In the illustrated embodiment the inner support structure 42 is generally rectangular and receives the reflector 26 therein. The inner support structure 42 may be, in turn, rotationally coupled to an outer support structure 46 by a pair of opposed, generally aligned torsion arms 48. In the illustrated embodiment the outer support structure 46 is generally rectangular and receives the inner support structure 42 therein. The outer torsion arms 48 are generally perpendicular to the inner torsion arms 44. Thus the reflector 26 may double gimbaled or otherwise pivotable about the two axes 38, 40 to position the reflector 26 as desired.

The reflector 26 may have or be coupled to a pair of opposed comb structures 50 that are interleaved with comb structures 52 of the inner support structure 42. Similarly, the inner support structure 42 may have or be coupled to a pair of opposed comb structures 54 that are interleaved with comb structures 56 of the outer support structure 46. A voltage can be applied to one or both comb structures 50, 52 to cause the reflector 26 to pivot about arms 44/axis 40. Similarly, a voltage can be applied to one or both comb structures 54, 56 to cause the reflector 26 to pivot about arms 48/axis 38. The voltages can be applied by a controller 58 (FIGS. 1 and 2) to thereby control movement and position of the reflector 26.

It should be noted that the arrangement of FIG. 4 illustrates an reflector 26 that is movable/oscillatable through the application of electrical forces by comb drives. However, the should be noted that electrical/electrostatic forces can be applied in a variety of manners besides comb drives. Moreover, beside electrical/electrostatic forces, various other forces may be utilized to drive the movement/oscillation of the reflector 26, such as magnetic, piezoelectric, or combinations of these drivers.

The range of motion of the reflector 26 can be selected as desired, but in one embodiment the reflector 26 is pivotable about the axis 38 by at least about 60 degrees in one case, and the reflector 26 is pivotable about the axis 40 at least about 60 degrees, or in another case at least about 40 degrees (with all angles being full angle values representing the full range of motion of the reflector 26).

In one embodiment the reflector 26 is moved such that the reflector 26 has a significantly higher frequency about one axis than about the other axis. For example, in one embodiment the reflector 26 is moved such that it has a frequency about the axis 40 that is at least about fifteen times greater, up to about 600 times or even greater, than the frequency of oscillation about the axis 38. In one embodiment the reflector 26 may have a frequency of about 19 kHz about the axis 40, and about 60 Hz about the axis 38.

Figure 5:
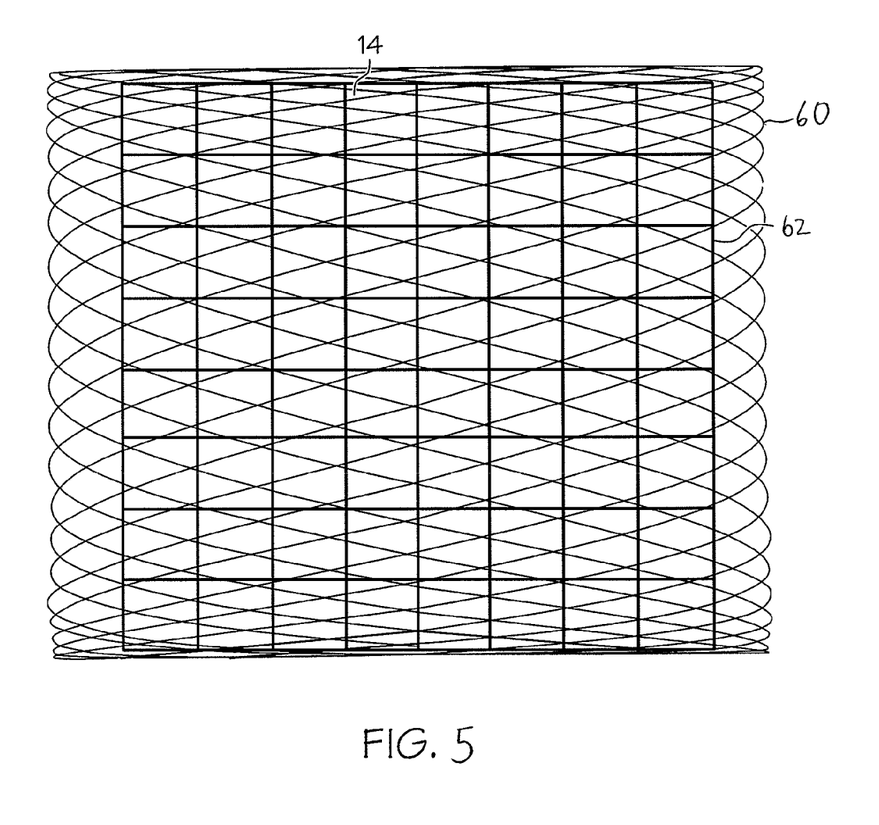
FIG. 5 is a representation of a path of scanned radiation provided by the scanning assembly of FIG. 1.

The reflector 26 may be moved about each axis 38, 40 in a reciprocating motion having a velocity profile that is generally sinusoidal to provide a bi-sinusoidal scan pattern. However, the velocity profile need not necessarily be at or close to sinusoidal. Furthermore, the reflector 26 may be oscillated at or close to resonant frequency about each axis 38, 40 (i.e. in a dual resonant manner). However, the frequency of oscillations can be at nearly any desired value to allow the reflected beam 22 to scan across the illuminated area 14 in the desired manner (such as in a progressive scan pattern). For example, FIG. 5 illustrates a classical Lissajous pattern 60 (imposed upon a grid 62) which may be scanned upon an area 14 during operation of the scanning unit 12. However, the scan pattern need not necessarily be implemented by a progressive scan pattern. Instead, the scan pattern can take any of a variety of other shapes or forms, including a spiral pattern scanned by a nutating mirror assembly, or a nutating or vibrating fiber, or other mechanism. In the case of a nutating or vibrating fiber, that component can be considered to be the movable element in place of the reflector 26.

The scanning unit 10 includes a collector 64, which collects/senses radiation emitted by the scanning unit 12 that is returned from the illuminated area 14. In the embodiment of FIG. 1 the collector 64 is configured coaxially within the housing 16 (see also FIG. 2). However, the collector 64 may take a variety of shapes and forms, and also need not necessarily be physically coupled to the housing 16. In any case the collector 64 should be located sufficiently close to the illuminated area 14 to effectively detect perturbed radiation.

The collector 64 may take any of a variety of forms, and in one embodiment includes a plurality of small diameter, multimode collecting fibers. The ends (or in some cases, the sides) of the fibers may be polished and arranged in a generally planar manner (or otherwise) to define an aperture. When the reflector 26/scanning unit 12 directs radiation 22 at the area 14, returned radiation impinges on the aperture, and the collecting fibers then conduct the received radiation to a radiation detector assembly 66. The radiation detector assembly 66/controller 58 may be operatively coupled to an image processor 67, which is in turn coupled to a display device 68 (such as a display screen, television screen, monitor, etc.) that can display a visual representation of the illuminated area 14 based upon data provided by the collector 64.

FIG. 6 schematically illustrates the operation of the reflector 26 in conjunction with the collector 64. The reflector 26 receives a beam of radiation 22 from the source fiber 18 and directs the beam 22 onto a surface or illuminated area 14. At a first point in time, the beam 22 deflected by the reflector 26 is in a position shown as 70, and impinges upon the surface to illuminate point 72. As the reflector 26 moves or oscillates about axis 40 (indicated by arrow A) at a later point in time the beam is in the position shown as 74 where the beam illuminates point 76. The directed radiation is reflected, absorbed, scattered, refracted or otherwise affected by the illuminated area 14, at least some of which is detected by the collector 64. The perturbed radiation may leave the area 14 in many directions and thus the collector 64 may only capture that fraction of reflected radiation which reaches its aperture.

Figure 2:
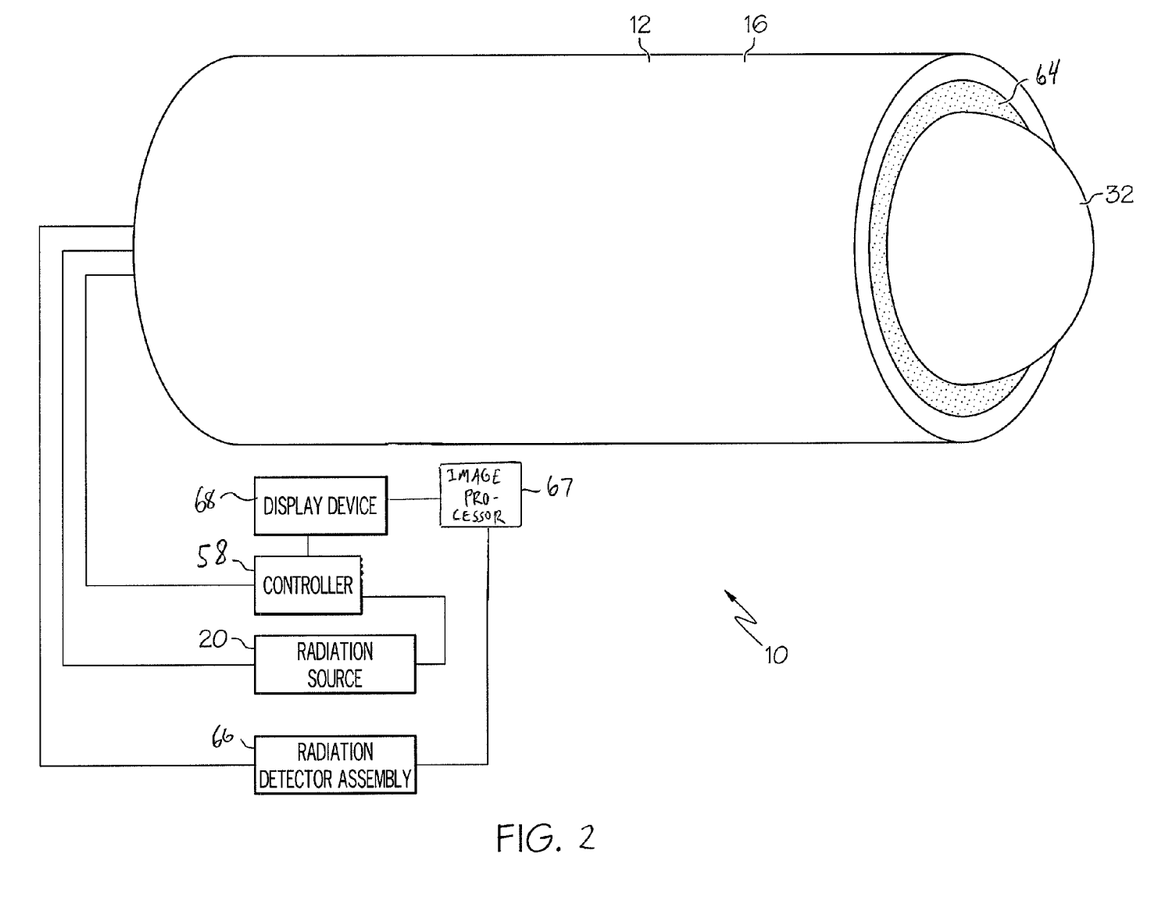
FIG. 2 is a front perspective view of the scanning assembly of FIG. 1.

Radiation that is intercepted by the collector 64 is passed to the radiation detector assembly 66 (FIGS. 1 and 2). The radiation detector assembly 66 may take the form of or include a bolometer, photodiode or avalanche photodiode that can output a series of electrical signals corresponding the power, amplitude, or other characteristic of each wavelength of radiation detected. The radiation detector assembly 66 may also include, or be coupled to, an analog-to-digital converter to convert the image data into a digital image signal stream. The signals can be used/processed by the image processor 67 (which could be, in one embodiment, part of the controller 58) to generate an image of the illuminated area 14 which can be displayed on a display device 68, or printed, stored, or further processed. The image can be generated by taking into consideration, for example, the position, angle, intensity and wavelength of beam 22 directed by the reflector 26, and the amount and/or wavelength of radiation sensed by the collector 50.

The housing 12 may constitute or include an elongate shaft (which can be either rigid or flexible) that is insertable into the body of a patient. The radiation source 20, controller 58, radiation detector assembly 66, image processor 67 and display device are 68 typically not insertable into the patient or carried in the housing 12, but are instead typically components positioned outside the body and accessible for use and viewing.

Figure 7:
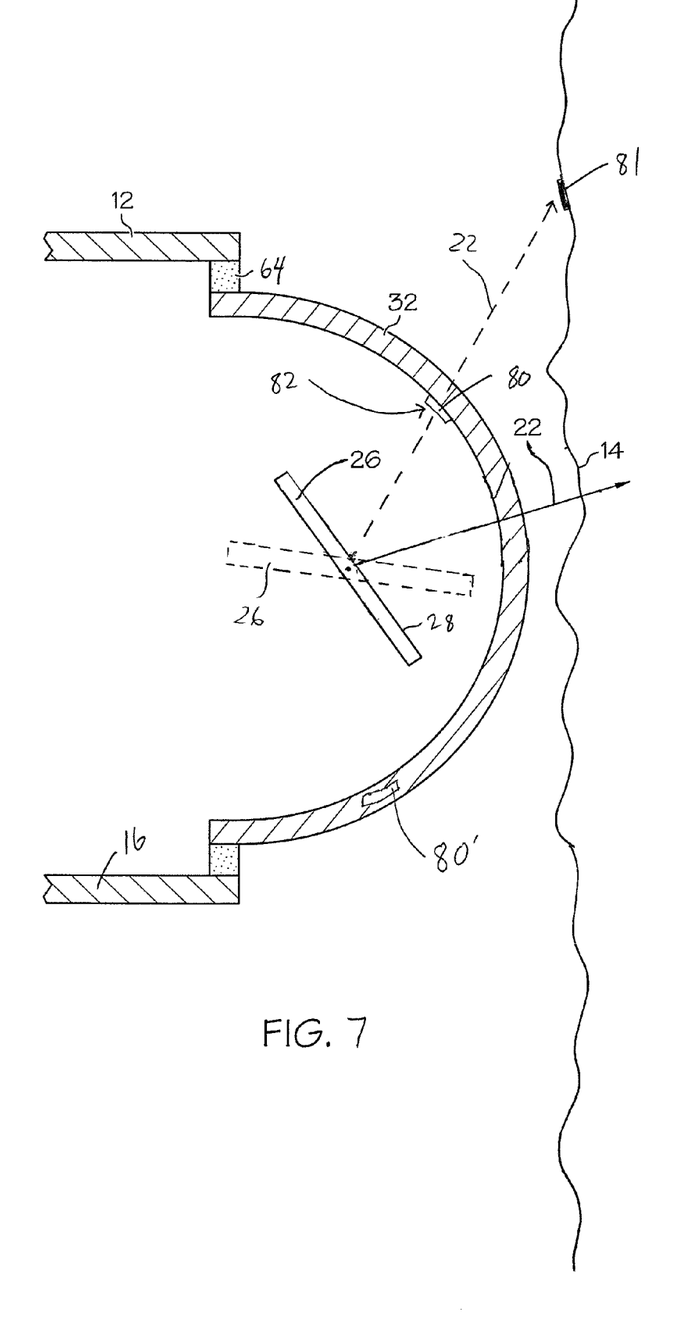
FIG. 7 is a side cross section of the distal end of the scanning assembly of FIG. 1, illustrating various reference marks.
Figure 8:
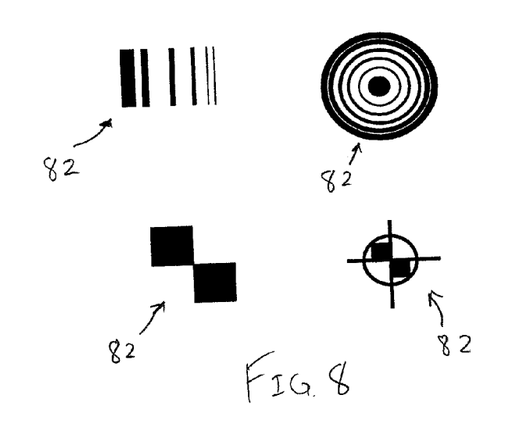
FIG. 8 illustrates various indicia which may be included in the reference marks.

In certain cases, it may be desired to track the position of the reflector 26 and thereby the trajectory of the beam 22, to aid in reconstruction of the image data. To that end a reference mark, reference marker, or auto correction marking ("ACM") 80 may be positioned to modulate the beam of radiation 22 after the beam 22 reflects off of the reflector 26, but before the beam 22 impinges upon the area of interest 14. For example, FIG. 7 illustrates a reference mark 80 positioned on the inner surface of the optical element 32. The reference mark 80 can have any variety of indicia, designs, patterns or the like 82 (collectively termed "indicia" herein) printed, positioned, or otherwise formed or located thereon. FIG. 8 illustrates some examples of differing indicia 82 that may be carried by the reference mark 80. The indicia 82 may be composed of high contrast patterns, geometric shapes or other designs of a type not expected to be found in the area of interest 14 to allow easy identification of the reference mark 80/indicia 82. The indicia 82 of the reference mark 80 may include portions that are generally opaque to the radiation 22.

As noted above, the reference mark 80 of FIG. 7 is positioned on the inner surface of the optical element 32. The reference mark 80 shown in FIG. 7 is at another position wherein the reference mark 80 is formed in, embedded in, laminated on, the optical element 32. The reference mark 80 can also be positioned on an outer surface of the optical element 32, or at other positions between the reflector 26 and the area of interest 14. The reference mark 80 may thus be positioned such that the radiation beam 22 impinges upon the reference mark 80 before the beam 22 entirely passes through the optical element 32.

When the reflector 26 is in its dotted line position shown in FIG. 7, the resultant radiation beam 22 may be directed as shown by the dotted line arrow. In this case, the reference mark 80 casts a shadow or a mask image 81 of its indicia 82 on the area of interest 14. Radiation that is returned from the area of interest 14 and detected by the collector 64 will thereby include the mask image (or more particularly, a distorted mask image) of the indicia 82 of the reference mark 80. The image processor 67 may be configured to recognize image data corresponding to the indicia 82 such that the position of the reflector 26/beam 22 can thereby be determined and tracked.

Figure 9:
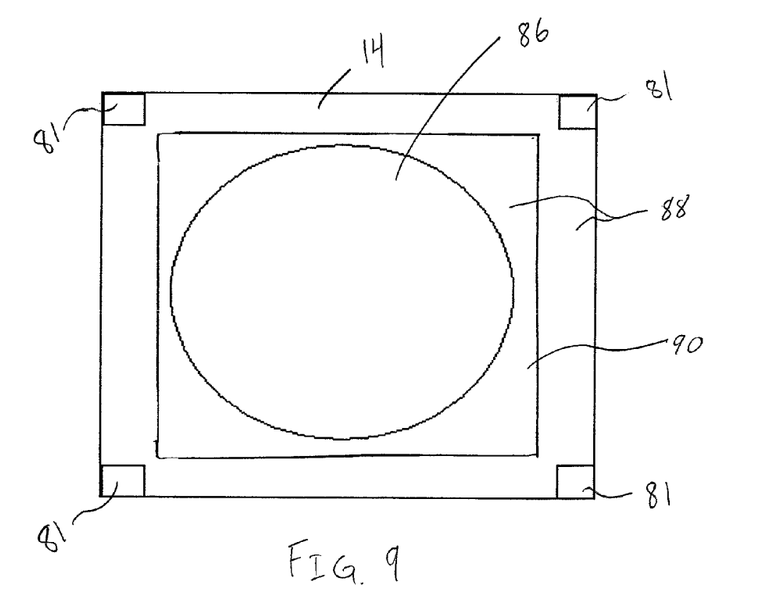
FIG. 9 is a front schematic view of a scanned area.

More particularly, assuming that the position of the reference mark 80 is known, when the reflector 26 directs the radiation beam 22 at the reference mark 80, the position of the reflector 26 at that moment can thereby be determined. If the scanning unit 12 includes multiple reference marks 80 (i.e. the four reference marks as shown in FIG. 9, although more or less reference marks 80 may be utilized as desired), then the position of the reflector 26/beam 22 at various points in space may be tracked. When more than one reference mark 80 is used, each reference mark 80 may have a unique indicia 82 to distinguish the reference marks 80 from each other.

The image processor 67 may use any of a variety of methods to recognize the reference mark(s) 80. In one embodiment, the image processor 67 has a filter incorporated therein that corresponds to some expected image data when the beam 22 is directed at the reference mark 80. In this manner, the filter's output is at a maximum when the return signal is identical to the expected image data. Thus when the filter output value is at a maximum (or within acceptable range of the maximum) the reference mark 80 can be considered to be located. The reference marks 80 can thus be identified without a need for full image reconstruction.

The use of the reference marks 80 to locate the position of the reflector 26 and/or beam 22 can be of great value in providing accurate reconstruction of the image of the area of interest 14. For example, although the voltage applied to the combs 50, 52, 54, 56 of FIG. 4 may be known, the response of the reflector 26 to the applied voltage is difficult to predict. More particularly, the controller 58 may apply periodic voltages, and the reflector 26 may need to be oscillated at desired magnitudes and in the desired phase/frequency. Once the position of the reflector 26 is known, various algorithms or feedback loops may be implemented to oscillate the reflector 26 in the desired manner. For example, in one case, the voltage applied to the combs 50/52 and/or 54/56 may be adjusted until a pattern of movement of the reflector 26 is detected. Next, the phase/frequency of the voltage applied to the combs can be adjusted until a stable movement pattern of the reflector 26 in the desired manner is achieved.

Thus, adjustment of the amplitude and phase of frequency of the drive voltages can be implemented to ensure high image quality and to accommodate for variables which can effect reflector movement, such as temperature variations, power supply drift and the like. Thus, various algorithms based upon feedback loops may be utilized to make adjustments in the drive signal. However, any of the wide variety of methods and algorithms may be utilized to adjust the drive signals, as desired, to provide known, predicted positions of the reflector 26.

Once the reflector 26 is oscillated in the desired manner, the position/trajectory of the beam 22 of any given time is also known. The position/trajectory of the beam 22 is then provided to the image processor 67, which can thereby reconstruct the image with accuracy since the image processor 67 can match image data received via the collector 64 with the trajectory and position of the beam 22 that generated the corresponding data. In other words, tracking the position of the reflector 26 allows the image processor 67 to link the time sequence of samples to the trajectory of the radiation beam 22. Accordingly, the reference mark 80 allows adjustments to be made by the image processor 67 in real time to provide a continuously optimized image.

One or more reference marks 80 may be positioned at or adjacent to the outer extent of the range of motion of the reflector 26 such that, for example, the mask images 81 of the reference marks 80 are positioned at the outer edge (in the corners) of the scanned area 14 (see FIG. 9). The "scanned area" can be considered the area that receives radiation during a full cycle of oscillations by the reflector 26. If desired, the reference marks 80 may be visible in the image displayed on the display device 68. In particular, it has been found that users of the scanning assembly 10 typically focus their attention on the central region 86 (which is circular in the illustrated embodiment of FIG. 9) of the scanned area 14. It has been found that users provide less attention to the peripheral region 88 (which is the area of the scanned area 14 outside the circular central region 86) of the scanned area 14. Accordingly, the reference marks 80 may be positioned in the outermost extent of the peripheral region 88 to be as unobtrusive as possible.

Rather than positioning the reference marks 80 to minimize their appearance, the image data may be filtered such that the part of the image data including the indicia 82 of the reference marks 80 is not displayed. For example, subset of the scanned area 14, termed the displayed area 90 (which is rectangular in the illustrated embodiment), may be displayed on the display device 68, while the portion of the scanned area 14 outside the displayed area 90 is not displayed. The displayed area 90 may be configured to exclude the reference marks 80. In this case, only a relatively small portion of the scanned area 14 is excluded, and the ACMs 80 do not intrude on the image as presented to the user on the display device 68.

In another embodiment, the entire scanned area 14 may be displayed on the display device 68, but the reference marks 80, or more accurately, the portion 81 of the area of interest 14 which is masked by the mark 80, is replaced with projected image data. In particular, image data immediately adjacent to the masked area 81 can be interpolated, extrapolated or otherwise manipulated (such as using Fourier transformations) to create a projected/synthesized image to replace the image date of the masked areas 81. In this manner, the "shadows" 81 of the reference marks 80 are effectively removed and replaced with projected image data.

In yet another embodiment, the reference marks 80 may be controlled such that the marks 80 are only intermittently positioned in the path of the radiation beam 22. In other words, the reference marks 80 may not be continuously present. For example, in one case the reference marks 80 may be intermittently moveable into and out of the path of the radiation beam 22 by mechanical means. Alternately, the reference marks 80 may be able to be switchable between a first state, wherein the reference mark 80 (or parts there of) is generally opaque to the radiation 22, and a second state wherein the reference mark 80 is generally transparent to the radiation 22. For example, the reference mark 80 may take the form of a liquid crystal display that can create a transient image of the indicia 82.

When the reference mark 80 is controlled in this manner, it may only be briefly viewable so as to not distract a viewer of the display device 68. For example, the reference mark 80 may be inserted so briefly as to not be visible to the human eye. A non-continuous reference mark 80 can also utilize the benefits of time multi-plexing and actual scene reflectivity. More particularly, in this case, actual scene data that corresponds to the otherwise masked area 81 of the reference mark from previous scans may be inserted to provide a generally continuous image to the viewer, similar to the method described above utilizing interpolation, extrapolation, Fourier transforms, etc.

The reference marks 80 may also be utilized to detect a loss of motion of the reflector 26. More particularly, because the image processor 67 continuously monitors the received data stream for the characteristic signature of the reference mark 80, a persistent lack of such a signature can be interpreted as a loss of motion of the reflector 26. When there is such a loss in motion, the radiation source 20 can quickly and immediately terminate emissions of the radiation beam 22. This rapid detection of loss of reflector motion provides a significant advantage by minimizing the possibility that the radiation source 20 will inadvertently damage the eyes of the operator or others nearby. Moreover, if it can be assured that the radiation source 20 can be operative in an eye-safe manner, the radiation source 20 may be operated at higher power levels which provides better signal-to-noise performance and image quality.

The reference marks 80 may also be utilized to provide normalization of color, or gray-scale, brightness, intensity or other optical properties of the image data. More particularly, the reference mark 80 may have known color, gray-scale or other physical/optical properties which can be stored in the image processor 67. In addition, the reference mark 80 may include portions that generally absorb the radiation of the beam 22 to provide a black level clamp to aid in image normalization. Alternately, the reference mark 80 may portions that are generally reflective, but which reflect the radiation to another area (i.e. somewhere in the housing 16 other than the receiver 64) which then absorbs the radiation to provide a black level clamp.

When the image data corresponding to the reference mark 80 is provided by the collector 64, the output of the image processor 67 can thereby be normalized such that the output data corresponds to the known/stored color, gray-scale, brightness, intensity, etc. data for the reference mark 80, or to process the black level clamp. In this manner, a true representation of color/gray-scale or other optical properties of the are of interest 14 can be provided. Thus, this technique helps to accommodate drifts in the system due to, for example, accumulation of dust, loss of radiation brightness, circuit drift, or other variables, and allows the system to provide a faithful reproduction of the area of interest 14. This technique, which is also analogous to the use of a black level clamp in television signals, may also allow DC restoration, thereby allowing the receiving circuits to be AC coupled to facilitate wide band processing.

In the embodiments described above, the reference mark 80 is positioned between the radiation beam 22 and the area of interest such that the reference mark 80 casts its shadow or mask image 81 on the area of interest 14. In an alternate embodiment shown in FIG. 10, the system is configured such that radiation 22 directed at the reference mark 80 is captured by the collector 64 before the radiation 22 impinges upon the area of interest 14 such that the captured radiation does not interact with the area of interest 14.

Figure 10:
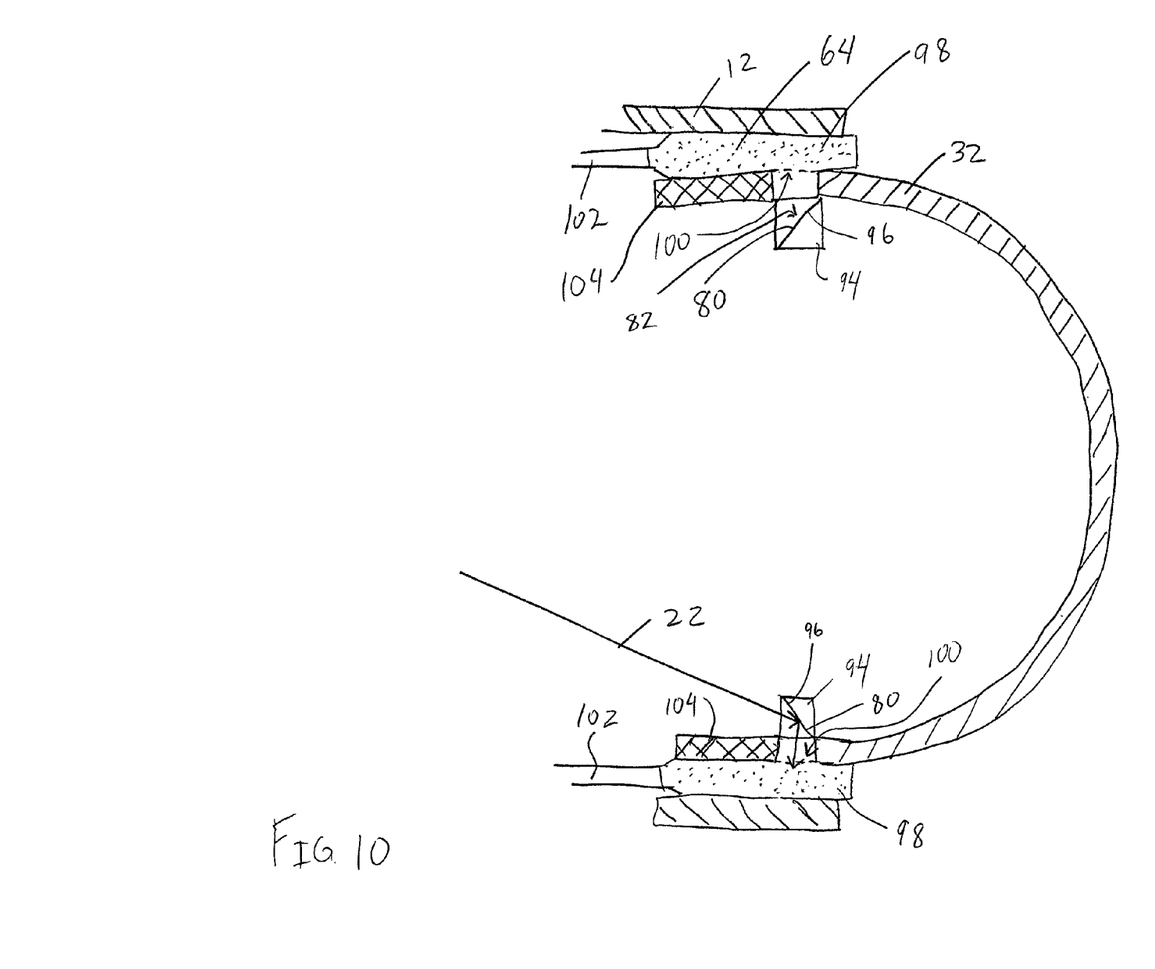
FIG. 10 is a side cross section of the distal end of a scanning assembly utilizing an alternate reference mark.

More particularly, in the embodiment of FIG. 10 the reference mark 80 is patterned on the internal reflective 96 surface of a prism 94, and the prism 94 is positioned adjacent an inner surface of the optical element 32. When the radiation beam 22 has a particular trajectory, (i.e. preferably at the outer edges of the swing of the reflector 26) the beam 22 impinges upon the internal reflective surface 96. The beam 22 is then reflected by the internal reflective surface 96 and routed directly into a light collection ring 98, which is optically coupled to an associated light collection fiber 102.

The light collection ring 98 may have a side access opening 100 which may be formed by, for example, abrading the circumferential surface of the light collection ring 98. The side access opening 100 allows the light collection ring 98 to receive radiation therein in a radial direction (i.e. as directed by the prism 94) in addition to receiving radiation at its axial end. Alternately, some of the collecting fibers may be directed towards surface 96. The radiation directed into the light collection ring 98 by the prism 94 is then directed in an axial manner down and towards the light collection fiber 102, and ultimately to the radiation detector assembly 66. A radiation baffle 104 may be positioned along the remaining length of the light collection ring 98 to prevent undesired reflections and radiation from entering the light collection ring 98. In the embodiment of FIG. 10, since the indicia 82 of the reference mark 80 is reflected directly into the optical collection ring 98, a high degree of coupling and a significantly improved signal to noise ratio is provided, which results in improved detection of the reference mark 80.

Rather than providing a prism to directly reflect the light into the side access opening 100 of the fiber 102, the reference mark 80 could be formed directly onto the inner surface of the optical element 32 and adjacent to the side access opening 100. In this case when the radiation beam 22 is directed at the reference mark 80, at least some of the radiation impinging upon the reference mark 32 is received through the side access opening 100 to allow the image processor 67 to detect the mark 80.

Figure 11:
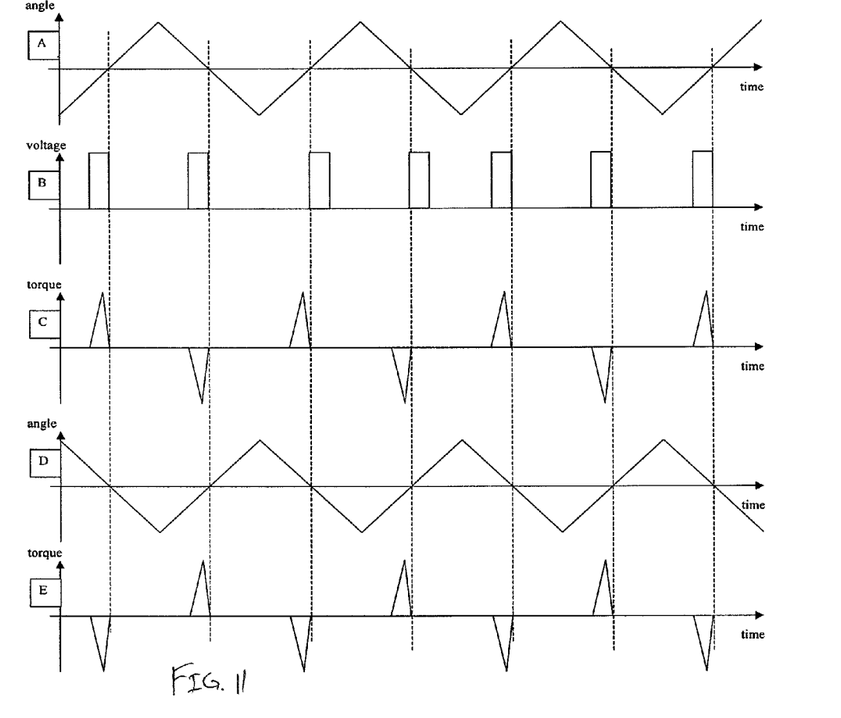
FIG. 11 is a series of graphs illustrating the relationship between a drive voltage and two cases of resultant torque and rotation.

The controller 58 may drive the reflector 26 by applying relatively short bursts of force/torque to the reflector 26. For example, when the reflector 26 is used in conjunction with the electrostatic comb drive mechanisms 50/52 and 54/56 of FIG. 4, voltages may be applied to the combs 50/52 and 54/56 in a rectangular pulse train, as shown in FIG. 11A. In this case, when a potential difference is applied to the combs 50/52 and/or 54/56 and the combs are sufficiently close, each comb is attracted to its associated, interleaving comb structure to move the reflector 26 as desired.

When the comb structures 50 and 52 or 54 and 56 are precisely co-planar, the force applied by the electrostatic drive voltage is applied in the direction of the plane, and therefore no torque or twisting force can be provided. In contrast, if the associated comb structures are not co-planar, a twisting force can be generated. Accordingly, if the moveable element (i.e. reflector 26 or inner support structure 42) is to be driven by the drive voltages, then typically the moveable element must rely on some coincidental perturbation to move the moveable element out of plane with the associated fixed element (i.e. inner support structure 42 or outer support structure 46). This coincidental perturbation may be provided by any variety of environmental sources, such as, for example, thermal forces, hand tremors, ambient vibrations, movement of the housing 16, etc.

However, when the system relies upon coincidental perturbation to provide the initial displacement, the resulting motion of the moveable element is unpredictable. For example, FIGS. 11A and 11C illustrate a first case showing rotation angular position and drive torque of a moveable element given the driven voltage of FIG. 11B. It should be noted that the angular position represented in FIG. 11A (and also FIG. 11D) is greatly simplified, and in a resonant system the rotation will in fact be generally sinusoidal. Moreover, a positive torque has been illustrated in FIG. 11 as causing a positive impulse of momentum, providing an instantaneous change in direction. The torque can be seen to increase rapidly as the movable element approaches the associated stationary comb, and then quickly falls to zero as the comb halves 50/52 or 54/56 become co-planar. In any case, the drive torque and angular position shown in FIGS. 11A and 11C show a first case of motion and torque that can result from the drive voltage of FIG. 11B. For example, this first case may arise when the moveable element was displaced out of plane in a first direction (i.e. "above" the plane) when the driving voltage was first applied.

In contrast, FIGS. 11D and 11E illustrate an alternate motion and drive torque that can result from the drive voltage of FIG. 11B. In this second case coincidental perturbation may have caused the moveable element to have been displaced out of plane in a second direction (i.e. "below" the plane) when the driving voltage was first applied. Thus, it can be seen that the resultant motion of the moveable element can be either in phase or out of phase with respect to the driving voltage wave form, depending upon the nature of the particular coincidental perturbation. Accordingly, in this case, the system must sense which of the two cases of motion is present and compensate in downstream data acquisition and processing.

The present system removes the ambiguity of motion by utilizing a mechanism or offset means for providing an initial offset of the moveable element in a known direction. This mechanism or offset means can take any of a variety of structures, systems or devices which move the moveable component outside its rest plane. The offset mechanism may be configured to move the moveable element out of place sufficiently to allow the associated electrostatic structure to apply sufficient forces to move the moveable element.

In one case, the offset means takes the form of a radial/torsional strain induced in the moveable element (i.e. the reflector 26 or inner support structure 42), or in the torsions arm 44, 48 supporting the associated moveable element. The strain may be induced or formed by any of a wide variety of methods, such as by a local heat treatment, local oxidation of a silicon surface, or by components having mismatched crystal structure that are deposited and shaped using patterning lithography. In this manner, for example, a strain may be induced in the torsion arm 44 to cause the reflector 26 to pivot slightly out of plane with respect to the inner support structure 42/comb structure 52.

Figure 12:
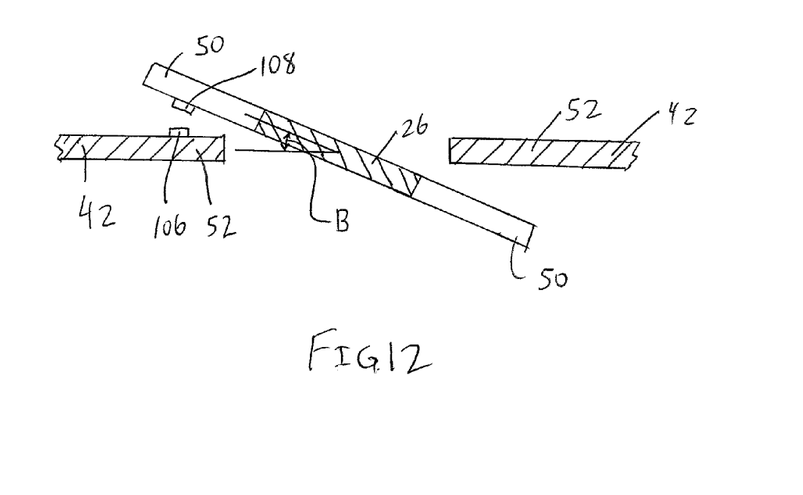
FIG. 12 is a side view of a drive mechanism utilizing an offset means.

The offset means may also take the form of magnets. For example, magnets of opposite polarity may be used, with one magnet being located on the moveable element and a corresponding magnet being located on the fixed element. The magnets can be formed and deposited in a variety of manners, such as by "hard" composition deposition, patterning, and/or magnetization during fabrication, possibly at the wafer level. FIG. 12 illustrates a first magnet 106 positioned on the fixed element (i.e. the inner support structure 42, or its comb structure 52, in this case), and a second magnet 108 positioned on the moveable element (i.e. the reflector 26, or more accurately its comb structure 50). The offset angle B provided by the offset means need not necessarily be as large as that shown in FIG. 12, but a relatively large offset angle B is shown for illustrative purposes. For example, in one embodiment the offset mechanism shifts the moveable element such that the moveable element is moved at least about 1.5 degree, or in another embodiment, at least about 1 degree, or even in another embodiment, at least about 0.5 degrees, out of the plane in which the moveable element rests in the absence of outside forces. Moreover, rather than utilizing two magnets 106, 108, one of the magnets 106, 108 may be replaced with a magnetizable material such as a ferrous material or the like.

The induced strain and magnetic structures described above can be considered to provide a "permanent" initial offset to the moveable element. However, the initial offset can also be provided by non-permanent or transient means, such as by the use of a high-energy radiation/laser beam. In this case, when an initial offset is desired, the radiation/laser beam can be operated to direct radiation at the moveable element, which causes movement thereof by the transfer of momentum due to photon impingement. Moreover, a transient initial offset could be provided by local asymmetrical heating (i.e. applied to the torsion arms 44/48) to cause uneven thermal expansion thereof, thereby inducing movement and the desired initial offset. In yet another case, a transient magnetic offset mechanism may be implemented by the use of a magnetized or magnetizable element positioned on one of the moveable/stationery elements, and electromagnet on the other of the moveable/stationery elements. A current can be passed through the electromagnet, thereby providing the desired initial offset by magnetic attraction/repulsion forces.

In this manner, the initial offset can be applied/induced to cause the moveable element to be moved/offset in a known, predictable direction. Thus, the known direction of the initial offset results in correspondingly predictable movement of the movable element, thereby providing simplified processing. In addition, the initial offset helps to reduce the time required to achieve the desired amplitude of motion (i.e. reduces start-up time required to get the movable element "up to speed.") The initial offset mechanism is believed to provide a condition wherein the movable element is displaced out of plane by a significantly greater amount than the movable element would be displaced by system perturbations. Thus the "starting" amplitude of the movable element is greater and is believed to reduce the time to achieve the full, desired amplitude of motion and improves stability in the movable element control system.

While the present invention has been illustrated by a description of several expressions of embodiments, it is not the intention of the applicants to restrict or limit the spirit and scope of the appended claims to such detail. Numerous other variations, changes, and substitutions will occur to those skilled in the art without departing from the scope of the invention. It will be understood that the foregoing description is provided by way of example, and that other modifications may occur to those skilled in the art without departing from the scope and spirit of the appended claims.

What is claimed is:

1. A scanned beam imaging system comprising:
    a radiation source configured to provide a beam of radiation;
    a movable element configured to direct said beam of radiation onto a scanned area;
    a collector configured to receive at least part of said radiation returned from the scanned area;
    a housing that houses said movable element therein;
    a reference mark coupled to or received in said housing and positioned such that at least part of said radiation from said radiation source is directable at said reference mark; and
    a processor operatively coupled to said collector and configured to recognize image data corresponding to said reference mark such that the position of said movable element can be determined.

2. The imaging system of claim 1 wherein said at least part of said radiation is directable at said reference mark by said movable element.

3. The imaging system of claim 1 wherein said reference mark is positioned such that a mask image of said reference mark is positioned at or adjacent to an outer edge of said scanned area.

4. The imaging system of claim 1 further including a controller operatively coupled to said movable element to control movement of said movable element, and said controller being operatively coupled to said processor such that said movable element can be oscillated in a desired manner.

5. The imaging system of claim 1 wherein said processor utilizes the position of said movable element to process the data from said collector and construct image data relating to said scanned area.

6. The imaging system of claim 1 wherein said processor is configured to generate predicted image data corresponding to a portion of said scanned area which is masked by said reference mark.

7. The imaging system of claim 1 wherein said housing includes an optical element forming an outer component of said housing which receives said beam of radiation there through, and wherein said reference mark is directly coupled to or integrated in said optical element.

8. The imaging system of claim 1 wherein said system is configured such that radiation directed at said reference mark is captured by said collector such that said captured radiation does not interact with said scanned area.

9. The imaging system of claim 1 further comprising a display device operatively coupled to said collector, said display device being configured to display a representation of radiation received by said collector to thereby display a representation of at least part of said scanned area.

10. The imaging system of claim 9 wherein said system is configured such that said display device displays a representation of only part of said scanned area, and wherein said displayed portion of said scanned area does not include areas of said scanned area upon which said reference mark is projected.

11. The imaging system of claim 1 further including a processor operatively coupled to said collector and configured to recognize image data corresponding to said reference mark, wherein said processor is configured to compare captured image data corresponding to said reference mark to stored values of the physical qualities of said reference mark for image normalization purposes.

12. The imaging system of claim 1 wherein said reference mark is controllable such that said reference mark is intermittently provided in the path of said radiation.

13. The imaging system of claim 1 wherein said reference mark includes portions that are generally opaque relative to said radiation.

14. The imaging system of claim 1 wherein said design includes indicia printed, positioned, or otherwise formed or located thereon, and wherein said indicia is of a type not expected to be found in the scanned area to allow easy identification of the reference mark.

15. The imaging system of claim 1 wherein said movable element is oscillatable about a first axis at a first frequency and a second perpendicular axis at a second frequency.

16. The imaging system of claim 1 wherein said housing is suitable for insertion into a body, and wherein said scanned area is tissue in said body.

17. The imaging system of claim 1 wherein said housing includes an optical element forming an outer component of said housing which receives said beam of radiation there through, said optical element including said reference mark, and wherein said reference mark is positioned such that at least part of said radiation from said radiation source is directable at said reference mark before said beam entirely passes through said optical element.

18. The imaging system of claim 1 wherein said moveable element is a reflector or an optical fiber.

19. A scanned beam imaging system comprising:
a housing suitable for insertion into a body;
a radiation source configured to provide a beam of radiation;
a movable element configured to direct said beam of radiation through said housing and onto an area within the body;
a reference mark coupled to or received in said housing and positioned such that at least part of said radiation from said radiation source is directable at said reference mark;
a collector configured to receive at least part of said radiation returned from the area within the body to aid in generating an image of said area within the body; and
a processor operatively coupled to said collector and configured to recognize image data corresponding to said reference mark such that at least one of the position of the movable element, or a trajectory of said beam of radiation, can be determined.

20. The imaging system of claim 19 wherein said movable element is positioned in said housing and configured to direct said beam of radiation onto said area within the body and at said reference mark.

21. A method for operating a scanned beam imaging system comprising:
providing a scanned beam imaging system including a housing, a radiation source, a movable element, a collector, and a reference mark which is positioned in or coupled to said housing;
causing said radiation source to emit a beam of radiation;
causing said movable element to direct said beam of radiation onto a scanned area;
causing said movable element to direct said beam of radiation at said reference mark;
operating said collector such that said collector receives at least part of said radiation returned from the scanned area; and
processing an output of said collector to recognize image data corresponding to said reference mark to thereby determine the position of said movable element in at least two dimensions.

22. The system of claim 1 wherein said reference mark is positioned at a point having a unique position known in three dimensions relative to said housing, and wherein said movable element is configured to direct said beam of radiation at said reference mark such that when said processor recognizes said image data said processor determines that said beam is intersecting said reference mark at said known position.

23. The system of claim 1 further comprising a supplemental reference mark coupled to or received in said housing and positioned such that at least part of said radiation from said radiation source is directable at said supplemental reference mark, wherein said supplemental reference mark is entirely discrete from and spaced apart from said reference mark, and wherein said reference mark and said supplemental reference mark include indicia that is unique relative to the other to distinguish the reference marks from each other.

* * * * *